United States Patent
Hershko et al.

(10) Patent No.: US 10,205,488 B2
(45) Date of Patent: Feb. 12, 2019

(54) LOW-POWER HIGH-ACCURACY CLOCK HARVESTING IN INDUCTIVE COUPLING SYSTEMS

(71) Applicant: Vectorious Medical Technologies Ltd., Tel-Aviv (IL)

(72) Inventors: Matan Hershko, Kiryat Ata (IL); Oren Goldshtein, Nahariya (IL); Aharon Daffan, Jerusalem (IL)

(73) Assignee: Vectorious Medical Technologies Ltd., Tel-Aviv (IL)

( * ) Notice: Subject to any disclaimer, the term of this patent is extended or adjusted under 35 U.S.C. 154(b) by 0 days.

(21) Appl. No.: 15/981,914

(22) Filed: May 17, 2018

(65) Prior Publication Data
US 2018/0269931 A1 Sep. 20, 2018

Related U.S. Application Data

(63) Continuation-in-part of application No. PCT/IB2015/060054, filed on Dec. 30, 2015, and a
(Continued)

(51) Int. Cl.
*H04B 5/00* (2006.01)
*H02J 50/12* (2016.01)
(Continued)

(52) U.S. Cl.
CPC .......... *H04B 5/0081* (2013.01); *H02J 50/12* (2016.02); *H04B 5/0037* (2013.01); *A61B 5/0215* (2013.01); *A61B 5/6869* (2013.01)

(58) Field of Classification Search
CPC ...... H04B 5/0081; H04B 5/0037; H02J 50/12
See application file for complete search history.

(56) References Cited

U.S. PATENT DOCUMENTS 3,264,861 A 8/1966 Miles
4,127,110 A 11/1978 Bullara
(Continued)

FOREIGN PATENT DOCUMENTS

JP S5973747 A 4/1984
KR 20040060577 A 7/2004
(Continued)

OTHER PUBLICATIONS

Bradford et al., "Wireless Power and Data Transmission for a Pressure Sensing Medical Implant", Proceedings BMT 2010, Rostock, Germany, 4 pages, Oct. 6-8, 2010.
(Continued)

*Primary Examiner* — Ayodeji O Ayotunde
(74) *Attorney, Agent, or Firm* — D. Kligler IP Services Ltd.

(57) ABSTRACT

An apparatus includes a front-end circuit and a digital processing circuit. The front-end circuit includes an antenna and a modulation switch. The digital processing circuit is configured to transmit data to a remote unit using inductive coupling of an Alternating Current (AC) magnetic field generated by the remote unit, by modulating a load impedance of the antenna using the modulation switch. The front-end circuit is configured to supply to the digital processing circuit a voltage signal, which has a frequency of the AC magnetic field and which has a non-zero envelope both during intervals in which the modulation switch is closed and during intervals in which the modulation switch is open, and wherein the digital processing circuit is configured to derive a clock signal from the voltage signal.

31 Claims, 3 Drawing Sheets

Related U.S. Application Data continuation-in-part of application No. 14/766,750, filed as application No. PCT/IB2014/060085 on Mar. 24, 2014, now Pat. No. 10,105,103.

(60) Provisional application No. 61/838,357, filed on Jun. 24, 2013, provisional application No. 61/813,575, filed on Apr. 18, 2013.

(51) Int. Cl.
*A61B 5/0215* (2006.01)
*A61B 5/00* (2006.01)

(56) References Cited

U.S. PATENT DOCUMENTS

| | | | |
|---|---|---|---|
| 4,206,761 A | 6/1980 | Cosman | |
| 4,237,900 A | 12/1980 | Schulman et al. | |
| 4,256,094 A | 3/1981 | Kapp et al. | |
| 4,377,851 A | 3/1983 | McNamara | |
| 4,432,372 A | 2/1984 | Monroe | |
| 4,519,401 A | 5/1985 | Ko et al. | |
| 4,743,836 A | 5/1988 | Grzybowski et al. | |
| 4,791,934 A | 12/1988 | Brunnett | |
| 4,881,939 A | 11/1989 | Newman | |
| 5,105,190 A | 4/1992 | Kip et al. | |
| 5,113,868 A | 5/1992 | Wise et al. | |
| 5,480,412 A | 1/1996 | Mouchawar et al. | |
| 5,493,470 A | 2/1996 | Zavracky et al. | |
| 5,514,171 A | 5/1996 | Hoegnelid et al. | |
| 5,564,434 A | 10/1996 | Halperin et al. | |
| 5,942,692 A | 4/1999 | Haase et al. | |
| 6,015,386 A | 1/2000 | Kensey et al. | |
| 6,025,725 A | 2/2000 | Gershenfeld et al. | |
| 6,051,853 A | 4/2000 | Shimada et al. | |
| 6,111,520 A | 8/2000 | Allen et al. | |
| 6,113,553 A | 9/2000 | Chubbuck | |
| 6,171,252 B1 | 1/2001 | Roberts | |
| 6,275,681 B1 | 8/2001 | Vega et al. | |
| 6,309,350 B1 | 10/2001 | Vantassel et al. | |
| 6,389,371 B1 | 5/2002 | Tsuchiya et al. | |
| 6,409,674 B1 | 6/2002 | Brockway et al. | |
| 6,622,041 B2 | 9/2003 | Terry, Jr. et al. | |
| 6,667,725 B1 | 12/2003 | Simons et al. | |
| 6,772,070 B2 | 8/2004 | Gilmanshin et al. | |
| 6,778,070 B1 | 8/2004 | Thomas | |
| 6,926,670 B2 | 8/2005 | Rich et al. | |
| 6,936,053 B1 | 8/2005 | Weiss | |
| 7,086,270 B2 | 8/2006 | Weinberg et al. | |
| 7,149,587 B2 | 12/2006 | Wardle et al. | |
| 7,216,048 B2 | 5/2007 | Wang et al. | |
| 7,256,695 B2 | 8/2007 | Hamel et al. | |
| 7,317,951 B2 | 1/2008 | Schneider et al. | |
| 7,335,161 B2 | 2/2008 | Von Arx et al. | |
| 7,413,547 B1 | 8/2008 | Lichtscheidl et al. | |
| 7,425,749 B2 | 9/2008 | Hartzell et al. | |
| 7,509,169 B2 | 3/2009 | Eigler et al. | |
| 7,515,971 B1 | 4/2009 | Doan | |
| 7,628,054 B2 | 12/2009 | Hajishah et al. | |
| 7,634,319 B2 | 12/2009 | Schneider et al. | |
| 7,635,338 B2 | 12/2009 | Eide | |
| 7,647,831 B2 | 1/2010 | Corcoran et al. | |
| 7,677,107 B2 | 3/2010 | Nunez et al. | |
| 7,678,123 B2 | 3/2010 | Chanduszko | |
| 7,684,872 B2 | 3/2010 | Carney et al. | |
| 7,686,768 B2 | 3/2010 | Bodecker et al. | |
| 7,762,138 B2 | 7/2010 | Zdeblick et al. | |
| 7,860,579 B2 | 12/2010 | Goetzinger et al. | |
| 7,899,550 B1 | 3/2011 | Doan et al. | |
| 8,021,307 B2 | 9/2011 | White et al. | |
| 8,118,749 B2 | 2/2012 | White et al. | |
| 8,154,389 B2 | 4/2012 | Rowland et al. | |
| 8,285,204 B2 | 10/2012 | Martin | |
| 8,353,841 B2 | 1/2013 | White et al. | |
| 8,355,777 B2 | 1/2013 | White et al. | |
| 8,406,358 B1 * | 3/2013 | Uehara | H04B 1/0028 375/260 |
| 8,432,265 B2 | 4/2013 | Rowland et al. | |
| 8,493,187 B2 | 7/2013 | Rowland et al. | |
| 8,810,405 B2 | 8/2014 | Stevenson et al. | |
| 8,894,582 B2 | 11/2014 | Nunez et al. | |
| 9,513,609 B2 | 12/2016 | Thueringer et al. | |
| 9,662,066 B2 | 5/2017 | Ledet et al. | |
| 9,730,764 B2 | 8/2017 | Van Der Weide et al. | |
| 2001/0018596 A1 | 8/2001 | Selmon et al. | |
| 2002/0045921 A1 | 4/2002 | Wolinsky et al. | |
| 2002/0077556 A1 | 6/2002 | Schwartz | |
| 2002/0120200 A1 | 8/2002 | Brockway et al. | |
| 2003/0097073 A1 | 5/2003 | Bullister et al. | |
| 2003/0139677 A1 | 7/2003 | Fonseca et al. | |
| 2004/0103906 A1 | 6/2004 | Schulman et al. | |
| 2005/0004644 A1 | 1/2005 | Kelsch et al. | |
| 2005/0065589 A1 | 3/2005 | Schneider et al. | |
| 2005/0088184 A1 | 4/2005 | Burdick et al. | |
| 2005/0288596 A1 | 12/2005 | Eigler et al. | |
| 2006/0116572 A1 | 6/2006 | Case | |
| 2006/0161364 A1 | 7/2006 | Wang et al. | |
| 2006/0206178 A1 | 9/2006 | Kim | |
| 2006/0229488 A1 | 10/2006 | Ayre et al. | |
| 2006/0287602 A1 | 12/2006 | O'Brien et al. | |
| 2007/0049980 A1 | 3/2007 | Zielinski et al. | |
| 2007/0049984 A1 | 3/2007 | Osypka | |
| 2007/0118038 A1 | 5/2007 | Bodecker et al. | |
| 2007/0135826 A1 | 6/2007 | Zaver et al. | |
| 2007/0142727 A1 | 6/2007 | Zhang et al. | |
| 2007/0179583 A1 | 8/2007 | Goetzinger et al. | |
| 2007/0255144 A1 | 11/2007 | Tulkki et al. | |
| 2007/0261496 A1 | 11/2007 | Jonsson et al. | |
| 2007/0293779 A1 | 12/2007 | Bardy | |
| 2008/0004673 A1 | 1/2008 | Rossing et al. | |
| 2008/0033527 A1 | 2/2008 | Nunez et al. | |
| 2008/0045242 A1 | 2/2008 | Dekock et al. | |
| 2008/0064966 A1 | 3/2008 | Brockway et al. | |
| 2008/0092663 A1 | 4/2008 | Corcoran et al. | |
| 2008/0139959 A1 | 6/2008 | Miethke et al. | |
| 2008/0154101 A1 | 6/2008 | Jain et al. | |
| 2008/0227487 A1 * | 9/2008 | Daniels | H04B 1/006 455/553.1 |
| 2008/0269573 A1 | 10/2008 | Najafi et al. | |
| 2008/0281212 A1 | 11/2008 | Nunez et al. | |
| 2009/0005859 A1 | 1/2009 | Keilman | |
| 2009/0013791 A1 | 1/2009 | Zdeblick et al. | |
| 2009/0024042 A1 | 1/2009 | Nunez et al. | |
| 2009/0030291 A1 | 1/2009 | O'Brien et al. | |
| 2009/0036754 A1 | 2/2009 | Pons et al. | |
| 2009/0069648 A1 | 3/2009 | Irazogui et al. | |
| 2009/0093729 A1 | 4/2009 | Zhang et al. | |
| 2009/0192381 A1 | 7/2009 | Brockway et al. | |
| 2009/0275924 A1 | 11/2009 | Lattanzio et al. | |
| 2009/0281520 A1 | 11/2009 | Highley et al. | |
| 2009/0299216 A1 | 12/2009 | Chen et al. | |
| 2010/0179449 A1 | 7/2010 | Chow et al. | |
| 2010/0179618 A1 | 7/2010 | Marnfeldt et al. | |
| 2010/0249756 A1 | 9/2010 | Koh | |
| 2010/0280330 A1 | 11/2010 | Samuelsson et al. | |
| 2011/0021887 A1 | 1/2011 | Crivelli et al. | |
| 2011/0040206 A1 | 2/2011 | Burger et al. | |
| 2011/0043336 A1 | 2/2011 | Gueorguiev | |
| 2011/0133894 A1 | 6/2011 | Henning et al. | |
| 2011/0160560 A1 | 6/2011 | Stone | |
| 2011/0264217 A1 | 10/2011 | Qureshi | |
| 2011/0303229 A1 | 12/2011 | Najafi et al. | |
| 2012/0022507 A1 | 1/2012 | Najafi et al. | |
| 2012/0319862 A1 | 12/2012 | Nagy et al. | |
| 2013/0107913 A1 | 5/2013 | Savoj | |
| 2013/0215979 A1 | 8/2013 | Yakovlev et al. | |
| 2013/0222153 A1 | 8/2013 | Rowland et al. | |
| 2013/0233086 A1 | 9/2013 | Besling et al. | |
| 2014/0028467 A1 | 1/2014 | Nagy et al. | |
| 2014/0062717 A1 | 3/2014 | Mudumbai et al. | |
| 2014/0155710 A1 | 6/2014 | Rowland et al. | |
| 2014/0306807 A1 | 10/2014 | Rowland et al. | |
| 2015/0282720 A1 | 10/2015 | Goldshtein et al. | |
| 2015/0290465 A1 | 10/2015 | Mashiach | |

(56) References Cited

U.S. PATENT DOCUMENTS

2016/0022216 A1 1/2016 Goldshtein et al.
2016/0058324 A1 3/2016 Cao et al.
2017/0018172 A1 1/2017 He et al.
2017/0118543 A1 4/2017 Ha et al.
2017/0155429 A1 6/2017 Hung et al.

FOREIGN PATENT DOCUMENTS

| | | | |
|---|---|---|---|
| WO | 2006042280 | A2 | 4/2006 |
| WO | 2008042229 | A2 | 4/2008 |
| WO | 2008127525 | A1 | 10/2008 |
| WO | 2009097485 | A1 | 8/2009 |
| WO | 2011053246 | A1 | 5/2011 |
| WO | 2012078861 | A2 | 6/2012 |
| WO | 2012090206 | A2 | 7/2012 |
| WO | 2014006471 | A2 | 1/2014 |
| WO | 2014145012 | A2 | 9/2014 |
| WO | 2014170771 | A1 | 10/2014 |

OTHER PUBLICATIONS

Dai et al., "Capacitive Micro Pressure Sensor Integrated with a Ring Oscillator Circuit on Chip", Sensors 2009, vol. 3, chapter 12, pp. 10158-10170, Jan. 1, 2009.

Yameogo et al., "Self Calibrating pressure sensor for biomedical applications", IEEE Sensors Conference, pp. 391- 694, Oct. 25-28, 2009.

Mandal et al., "Power-Efficient Impedance-Modulation Wireless Data Links for Biomedical Implants", IEEE Transactions on Biomedical Circuits and Systems, vol. 2, No. 4, pp. 301-315, Dec. 4, 2008.

Olivo et al., "Electronic implants: Power delivery and management", Integrated Systems Laboratory—EPFL, 6 pages, Mar. 22, 2013.

Ziaie et al., "An Implantable Microsystem for Tonometric Blood Pressure Measurement", Biomedical Microdevices, vol. 3, Issue 4, pp. 285-292, Dec. 2001.

Cleven et al., "A Novel Fully Implantable Wireless Sensor System for Monitoring Hypertension Patients", IEEE Transactions on Biomedical Engineering vol. 59, No. 11, pp. 3124-3130, Nov. 2012.

Jiang., "Design challenges of implantable pressure monitoring system", Frontiers of Neuroscience, vol. 4, Art 29, pp. 1-4, Feb. 26, 2010.

Simons et al., "Spiral chip implantable radiator and printed loop external receptor for RF telemetry in bio-sensor systems", In Radion and Wireless Conference IEEE, 12 pages, 2004.

Simons et al., "Wearable wireless telemetry system for implantable bio-MEMS sensors", In Engineering in Medicine and Biology Society Conference, IEEE, 12 pages, 2006.

Maxim, "Approaches for Compensating Span and Offset in Pressure Sensors", Application Note 743, 5 pages, Mar. 27, 2001.

Coosemans., "An autonomous bladder pressure monitoring system", Katholike Universiteit Leuven, Department ESAT-MICAS, Kasteelpark Arenberg, Belgium, Sensors and Actuators A: Physical, Elsevier BV, vol. 123-124, pp. 155-161, Sep. 23, 2005.

\* cited by examiner

LOW-POWER HIGH-ACCURACY CLOCK HARVESTING IN INDUCTIVE COUPLING SYSTEMS

CROSS-REFERENCE TO RELATED APPLICATIONS

This application is a continuation in part of U.S. patent application Ser. No. 14/766,750, filed Aug. 9, 2015. This application is also a continuation in part of PCT Application PCT/IB2015/060054, filed Dec. 30, 2015. The disclosures of these related applications are incorporated herein by reference.

FIELD OF THE INVENTION

The present invention relates generally to inductive coupling clock-less systems such as medical implants, and methods, and particularly to methods and systems configured for operating by way of clock-signal harvesting.

BACKGROUND OF THE INVENTION

Inductive coupling is used as a means for communication and for providing electrical power in various systems, such as in medical implants. For example, PCT International Publication WO 2014/170771 describes an implant including an antenna, circuitry, and a voltage clamping element. The antenna is configured to communicate with an external unit using inductive coupling of a magnetic field. The circuitry is configured to produce data for transmission to the external unit, to modulate a load impedance applied to the antenna as a function of the data so as to transmit the data, and to receive electrical power from the magnetic field via the antenna for powering the circuitry. The voltage clamping element is coupled to clamp a voltage induced by the magnetic field across the antenna so as to maximize a modulation depth of the load impedance, and so as to regulate the electrical power that powers the circuitry.

SUMMARY OF THE INVENTION

An embodiment of the present invention that is described herein provides an apparatus including a front-end circuit and a digital processing circuit. The front-end circuit includes an antenna and a modulation switch. The digital processing circuit is configured to transmit data to a remote unit using inductive coupling of an Alternating Current (AC) magnetic field generated by the remote unit, by modulating a load impedance of the antenna using the modulation switch. The front-end circuit is configured to supply to the digital processing circuit a voltage signal, which has a frequency of the AC magnetic field and which has a non-zero envelope both during intervals in which the modulation switch is closed and during intervals in which the modulation switch is open, and wherein the digital processing circuit is configured to derive a clock signal from the voltage signal.

In some embodiments, the front-end circuit includes a voltage clamping element connected in series with the modulation switch. In an embodiment, the front-end circuit further includes a diode connected in series with the modulation switch. In an example embodiment, the antenna is connected in parallel to the serially-connected modulation switch and voltage clamping element.

In another embodiment, the voltage clamping element is configured to clamp a voltage signal induced by the AC magnetic field across the antenna, and the front-end circuit is configured to provide the clamped voltage signal for powering the digital processing circuit from a connection point between the modulation switch and the voltage clamping element. In yet another embodiment, the voltage clamping element includes a transistor biased by a Zener diode.

Typically, the digital processing circuit is configured to derive the clock signal solely from the voltage signal without an oscillator and/or a Phase-Locked Loop (PLL). In some embodiments, the apparatus includes a pressure sensor, and the digital processing circuit is configured to read a pressure reading from the pressure sensor, and to transmit the pressure reading to the remote unit using the derived clock signal.

In a disclosed embodiment, the antenna includes a coil. In an embodiment, the front-end circuit includes a capacitor connected in parallel with the coil. In another embodiment, the digital processing circuit is configured to modulate the load impedance by alternately opening and closing the modulation switch in a pattern that depends on the data. In some embodiments, the digital processing circuit is configured to derive the clock signal from the voltage signal both during the intervals in which the modulation switch is closed and during the intervals in which the modulation switch is open.

There is additionally provided, in accordance with an embodiment of the present invention, a method including, using a digital processing circuit, transmitting data to a remote unit using inductive coupling of an Alternating Current (AC) magnetic field generated by the remote unit, by modulating a load impedance of an antenna using a modulation switch. A voltage signal, which has a frequency of the AC magnetic field and which has a non-zero envelope both during intervals in which the modulation switch is closed and during intervals in which the modulation switch is open, is supplied to the digital processing circuit. A clock signal is derived from the voltage signal in the digital processing circuit.

There is further provided, in accordance with an embodiment of the present invention, a method including applying an external unit to form a magnetic field, having a frequency and an accuracy, around a remote system comprising a modulation switch and a digital processing circuit. A clock signal, having the frequency and the accuracy, is derived in the remote system from the magnetic field. The digital processing circuit is applied to generate a digital signal carrying data synchronized with the clock signal. The digital processing circuit is applied to manipulate the modulation switch in a series of alternations between an open state and a closed state in a pattern derived from the digital signal, thereby encoding the data by way of load modulation. The external unit is applied to decode the data by extracting the load modulation with the clock signal.

In some embodiments, the method includes powering the digital processing circuit solely from the magnetic field by way of inductive coupling. In an embodiment, deriving the clock signal is performed both during intervals in which the modulation switch is in the closed state and during intervals in which the modulation switch is in the open state. In another embodiment, a voltage clamping element is connected in series with the modulation switch. In a disclosed embodiment, a diode is connected in series with the modulation switch. In an example embodiment, an antenna of the remote system is connected in parallel to the serially-connected modulation switch and voltage clamping element. In some embodiments, the method includes clamping, using the voltage clamping element, a voltage signal induced by the magnetic field across the antenna, and providing the clamped voltage signal for powering the digital processing circuit from a connection point between the modulation switch and the voltage clamping element.

The present invention will be more fully understood from the following detailed description of the embodiments thereof, taken together with the drawings in which:

DETAILED DESCRIPTION OF EMBODIMENTS

Overview

Figure 1:
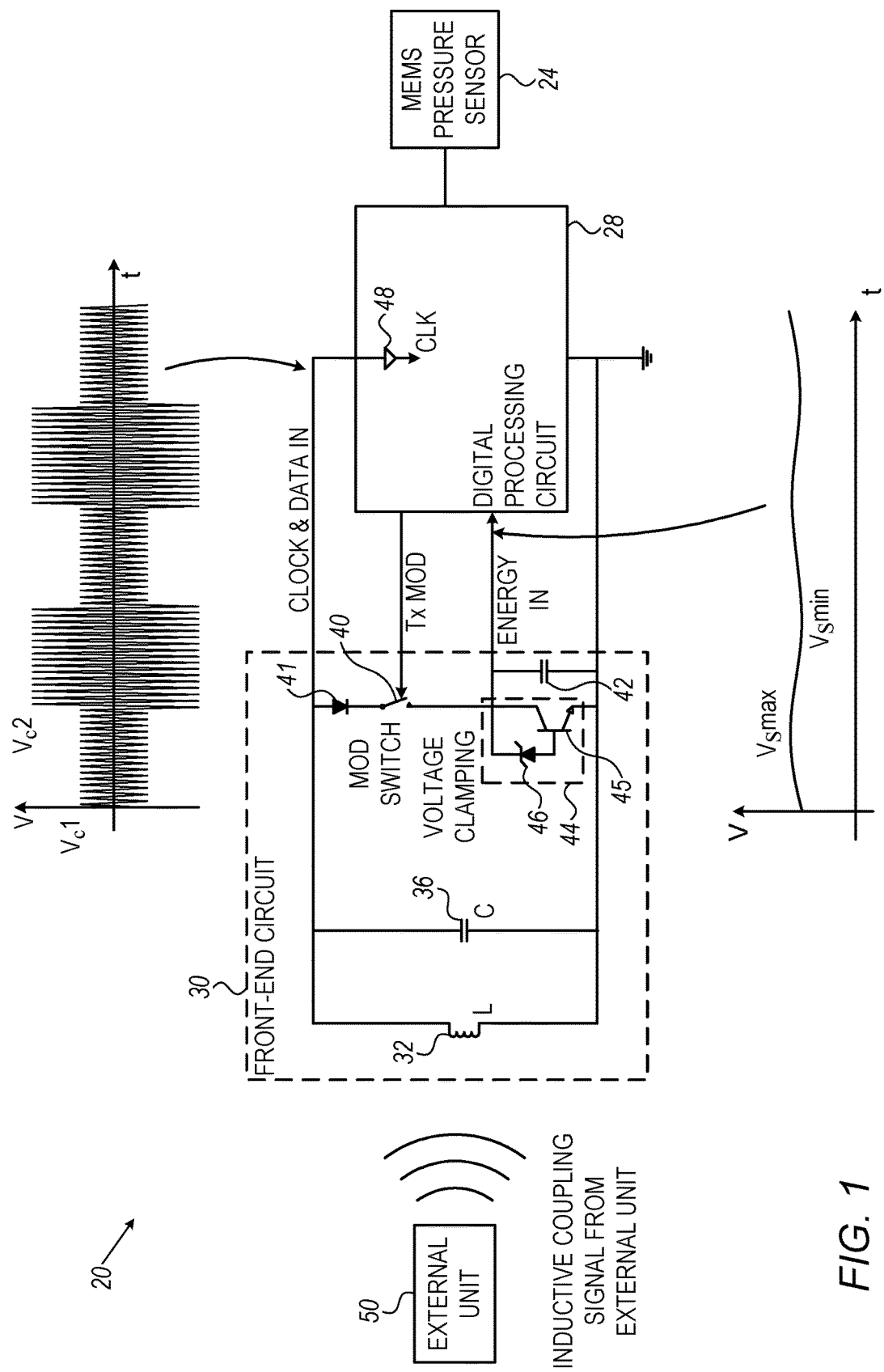
FIG. 1 is a block diagram that schematically illustrates a system (e.g., an implant) for measuring pressures (e.g., sensing blood pressure in the cardiovascular system) remotely to an external unit, in accordance with an embodiment of the present invention.

Embodiments of the present invention that are described herein provide improved methods and apparatus for clock signal harvesting in inductive-coupling systems. The embodiments described herein refer mainly to devices that are implanted in the cardiovascular system, measure ambient blood pressure and communicate with an external unit. The disclosed techniques, however, are applicable in various other systems and applications.

In some embodiments, a sensory implant is positioned in the cardiovascular system of a patient and communicates with an external unit using inductive coupling. The external unit generates an Alternating Current (AC) magnetic field, which is used both for communication and for supplying energy to the implant. The implant comprises a front-end circuit, which comprises an antenna and a modulation switch. The implant further comprises a digital processing circuit that transmits blood-pressure readings and other data to the remote unit by modulating the load impedance of the antenna using the modulation 'on/off' switch.

In the embodiments described herein, the digital processing circuit is clocked by a clock signal that is derived directly from the carrier of the AC magnetic field generated by the external unit. In some embodiments, the front-end circuit of the implant has a unique topology, which enables it to supply to the digital processing circuit a voltage signal, which has the same frequency as the AC magnetic field and has a non-zero envelope both during intervals in which the modulation switch is open, and during intervals in which the modulation switch is closed.

The digital processing circuit derives its clock signal from this voltage signal, both during the intervals in which the modulation switch is open, and during the intervals in which the modulation switch is closed. This capability is in sharp contrast to other possible inductive coupling schemes, in which the modulation switch short-circuits the antenna when closed.

In an example embodiment, the front-end circuit comprises a voltage clamping element that fixes the voltage and is connected in series with the modulation switch. The antenna is connected in parallel to the serially-connected modulation switch and voltage clamping element. Energy supply for the digital processing circuit is taken from the connection point between the modulation switch and the voltage clamping element. The voltage signal from which the clock signal is extracted, on the other hand, is taken directly from across the antenna.

When using this topology, as long as the external unit induces a magnetic field for receiving data from the implant, the envelope of the voltage signal provided to the digital processing circuit retains a non-zero average value regardless of whether the modulation switch is open or closed. As a result, the digital processing circuit is able to derive the clock signal directly from the voltage signal independently to operation of the modulation switch and/or clamping element.

The disclosed clock harvesting scheme enables the implant to derive its clock signal directly from the AC magnetic field of the external unit, without a need for any sort of local oscillator, Phase-Locked Loop (PLL) or similar components. As such, the size, cost and power consumption of the implant are reduced considerably relative to similar sensory implants equipped with any type of accurate internal clock source, and the reliability of the implant is maintained or is even improved relative thereto. Moreover, since the clock signal in the implant tracks the frequency of the AC magnetic field directly, rather than being locked on it, the clock signal is free of additional phase noise, jitter and other possible impairments.

Furthermore, unlike solutions in which the clock accuracy of the implant depends on the performance of a local oscillator, in the disclosed clock harvesting solution the clock accuracy of the implant is dictated directly by the clock accuracy of the external unit. Therefore, for example, in the disclosed solution the clock accuracy of the implant does not influence the implant's energy consumption due to the fact that it is not generated internally.

System Description

FIG. 1 is a block diagram that schematically illustrates an apparatus in a form of an implant 20 configured for sensing blood pressure in the cardiovascular system, for example in the heart or in the pulmonary artery, in accordance with an embodiment of the present invention. Implant 20 is implanted in the cardiovascular system of a patient and measures the ambient blood pressure. Implant 20 communicates with a remote external unit 50, and receives energy supply from the external unit, using magnetic-field inductive coupling.

In some embodiments, implant 20 comprises a capacitive Micro-Electro-Mechanical Systems (MEMS) pressure sensor 24, a digital processing circuit 28 and a front-end circuit 30. Sensor 24 is applicable for measuring the ambient blood pressure by producing an output derived from change of capacitance indicative of change in ambient pressure. Digital processing circuit 28, among other tasks, converts the output of sensor 24 into a digital signal sufficient/applicable for transmission.

The external unit generates an Alternating Current (AC) magnetic field, which is induced in an antenna coil 32 in front-end circuit 30. Digital processing circuit 28 modulates the load impedance of the antenna, which in turn modulates the induced magnetic field, so as to transmit data (e.g., the sensor output) to the external unit. The induced magnetic field is also used for supplying electrical power for powering digital processing circuit 28, and for supplying a clock signal for clocking digital processing circuit 28. Optionally, the induced magnetic field may also be used for transmitting data from the external unit to implant 20.

In the example of FIG. 1, front-end circuit 30 comprises antenna coil 32, also referred to herein as "antenna" for brevity. A capacitor 36 is connected in parallel with antenna coil 32, so as to form a parallel resonant circuit. Typically, the resonance frequency of this resonant circuit is set to match the frequency of the magnetic field generated by the external unit. The resonant circuit typically has a high Q factor, i.e., a sharp resonance curve. This feature increases the sensitivity of circuit 30.

Front-end circuit 30 further comprises a modulation switch 40, a voltage clamping element 44 and a diode 41 that are connected in series with one another. Diode 41 rectifies the voltage induced across the antenna, so that electrical current flows only in one direction (top to bottom in the figure). With respect to the direction of current flow, diode 41 precedes switch 40, and clamping element 44 follows switch 40. The cascaded (serially-connected) switch 40, voltage clamping element 44 and diode 41 are connected in parallel with antenna 32. Switch 40, voltage clamping element 44 and diode 41 can be regarded collectively as a "switch circuit," which may comprise additional components and perform additional functions.

Digital processing circuit 28 transmits data to the external unit by modulating switch 40 with the digital signal. In the present context, the term "modulating the switch" means alternately opening and closing the switch in a pattern that depends on the data.

Voltage clamping element 44 clamps the voltage induced by the magnetic field across antenna 32 to a suitable and accurate supply voltage for powering digital processing circuit 28. In the example of FIG. 1, voltage clamping element 44 comprises a transistor 45 that is biased by a Zener diode 46. The principles of operation of this configuration are described further below. Alternative configurations are also described.

As can be seen in FIG. 1, in the disclosed embodiment the energy supply for digital processing circuit 28 (denoted "ENERGY IN") is taken from the connection point between switch 40 and voltage clamping element 44. A capacitor 42 low-pass filters the variations in energy supply occurring due to modulation of switch 40. The voltage signal from which circuit 28 derives ("harvests") a clock signal, on the other hand, is taken directly from across antenna 32.

In the present example, digital processing circuit 28 comprises a buffer 48 that is configured to convert the voltage signal into a digital square-wave clock signal (denoted "CLK"). The clock signal has nominal logic levels as specified for the digital circuitry being clocked. Buffer 48 may comprise, for example, a comparator that compares the voltage signal to a threshold. If the voltage signal is below the threshold, the comparator outputs a voltage corresponding to "logic 0". If the voltage signal is above the threshold, the comparator outputs a voltage corresponding to "logic 1". In some embodiments the threshold is preset, e.g., to zero. In other embodiments, circuit 28 may comprise logic that adapts the threshold, e.g., for compensating for DC offset in the voltage signal and/or for creating a more balanced clock signal with a duty cycle closer to 50%.

The configuration of implant 20 shown in FIG. 1 is an example configuration, which is chosen purely for the sake of conceptual clarity. In alternative embodiments, any other suitable device configuration can be used. Elements of implant 20 that are not mandatory for understanding of the disclosed techniques have been omitted from the figure for the sake of clarity.

Example implementations of such implants and their circuitry are described, for example, in U.S. patent application Ser. No. 14/766,750 and PCT Application PCT/IB2015/060054, cited above. Further aspects relating to drift compensation in such implants are addressed in PCT Application PCT/IB2013/060038, filed Nov. 10, 2013, which is assigned to the assignee of the present patent application and whose disclosure is incorporated herein by reference.

The different elements of implant 20 may be implemented using suitable hardware, such as in one or more RFICs, microprocessors, Application-Specific Integrated Circuits (ASICs) or Field-Programmable Gate Arrays (FPGAs). In some embodiments, some elements of device 20, e.g., certain functions of digital processing circuit 28, can be implemented using software, or using a combination of hardware and software elements.

Clock Harvesting without PLL or Local Oscillator in Implant

As noted above, the magnetic field generated by the external unit is typically an AC field. In an example embodiment, the magnetic field is sinusoidal and has a frequency of 6.78 MHz. Among other tasks, front-end circuit 30 is configured to provide the voltage signal, which is induced in antenna 32 by this magnetic field, to digital processing circuit 28. The voltage signal has the frequency of the AC magnetic field generated by external unit 50. Circuit 28 reconstructs, from the voltage signal, a clock signal having the same frequency. The clock signal is used for clocking the digital circuitry in circuit 28.

In particular, the topology of front-end circuit 30 enables the front-end circuit to provide a continuous, uninterrupted clock signal to digital processing circuit 28, in spite of the modulation applied by switch 40. In the present context, the term "uninterrupted" means that the clock signal is provided both when the modulation switch is closed and when the modulation switch is open.

To demonstrate this feature, a graph at the top of FIG. 1 shows the voltage signal (denoted "CLOCK & DATA IN") that is provided to circuit 28. The voltage signal comprises a sinusoidal carrier having a frequency of 6.78 MHz. The envelope of the voltage signal alternates between two voltage levels $V_c1$ and $V_c2$ as a result of the modulation of switch 40 by circuit 28. When switch 40 is closed, the voltage signal is set to the lower value $V_c1$. When switch 40 is open, the voltage signal is set to the higher value $V_c2$.

It is noted that, even though the magnitude of the envelope of the voltage signal alternates between $V_c1$ and $V_c2$ in response to the load modulation, the envelope is non-zero. This feature is achieved by the unique topology of front-end circuit 30, in which modulation switch 40 does not form an electrical short across antenna 32 when closed. Instead, switch 40 is connected in series with voltage clamping element 44, and the cascade of the switch and clamping element is connected across the antenna. As a result, circuit 30 provides a continuous, uninterrupted 6.78 MHz carrier to circuit 28, both during intervals in which switch 40 is closed and during intervals in which switch 40 is open.

Voltage clamping element 44 plays a dual role in this configuration. The first role, as explained above, is to prevent short-circuit across the antenna during intervals in which switch 40 is closed (i.e., to ascertain that the envelope of the voltage signal provided to circuit 28 is always non-zero). The second role is to clamp and regulate the energy supply to circuit 28.

To demonstrate the latter feature, a graph at the bottom of FIG. 1 shows the voltage provided to digital processing circuit 28 from the connection point between switch 40 and voltage clamping element 44. As can be seen in the graph, the supply voltage has relatively small variations between a minimal voltage $V_s$min and a maximal voltage $V_s$max.

In the example of FIG. 1, voltage clamping element 44 comprises a parallel regulator or stabilizer, which comprises a transistor 45 (in the present embodiment a Bipolar Junction Transistor—BJT) and a Zener diode 46. When modulation switch 40 is closed, the voltage induced in antenna coil 32 falls across the collector-emitter of transistor 45, and also across diode 46. When this voltage reaches the breakdown voltage (Zener voltage) of diode 46, the diode begins to conduct. As a result, transistor 46 is switched-on, i.e., begins to conduct current between its collector and emitter.

In the above implementation, voltage clamping element 44 is a relatively narrowband device having a relatively slow response. As such, voltage clamping element 44 reacts to the relatively slow modulation rate of switch 40, but not to the higher rate of the carrier frequency. The former rate is typically on the order of KHz (e.g., 20 KHz), whereas the latter rate is on the order of MHz (e.g., 6.78 MHz).

The configuration of voltage clamping element 44 shown in FIG. 1 is a simplified example configuration that is depicted purely for the sake of conceptual clarity. In alternative embodiments, any other suitable configuration can be used. Alternative examples of voltage clamping elements may comprise, for example, a Zener diode, a cascade of multiple silicon diodes, Schottky diodes and/or Zener diodes, various transistor-based voltage-clamping circuits, or any other suitable implementations. Such implementations are described, for example, in U.S. patent application Ser. No. 14/766,750, cited above.

Since the envelope of the voltage signal ("CLOCK & DATA IN") is always non-zero, the clock signal ("CLK") at the output of buffer 48 is continuous and has no interruptions. As such, the CLK signal is used directly, as-is, for clocking circuit 28, without a need for any sort of local oscillator, Phase-Locked Loop (PLL) or similar circuitry. In some embodiments, for extra safety, circuit 28 comprises logic that compensates for temporary loss of one or more clock pulses in the "CLK" signal. This mechanism, however, is in no way mandatory.

Figure 2:
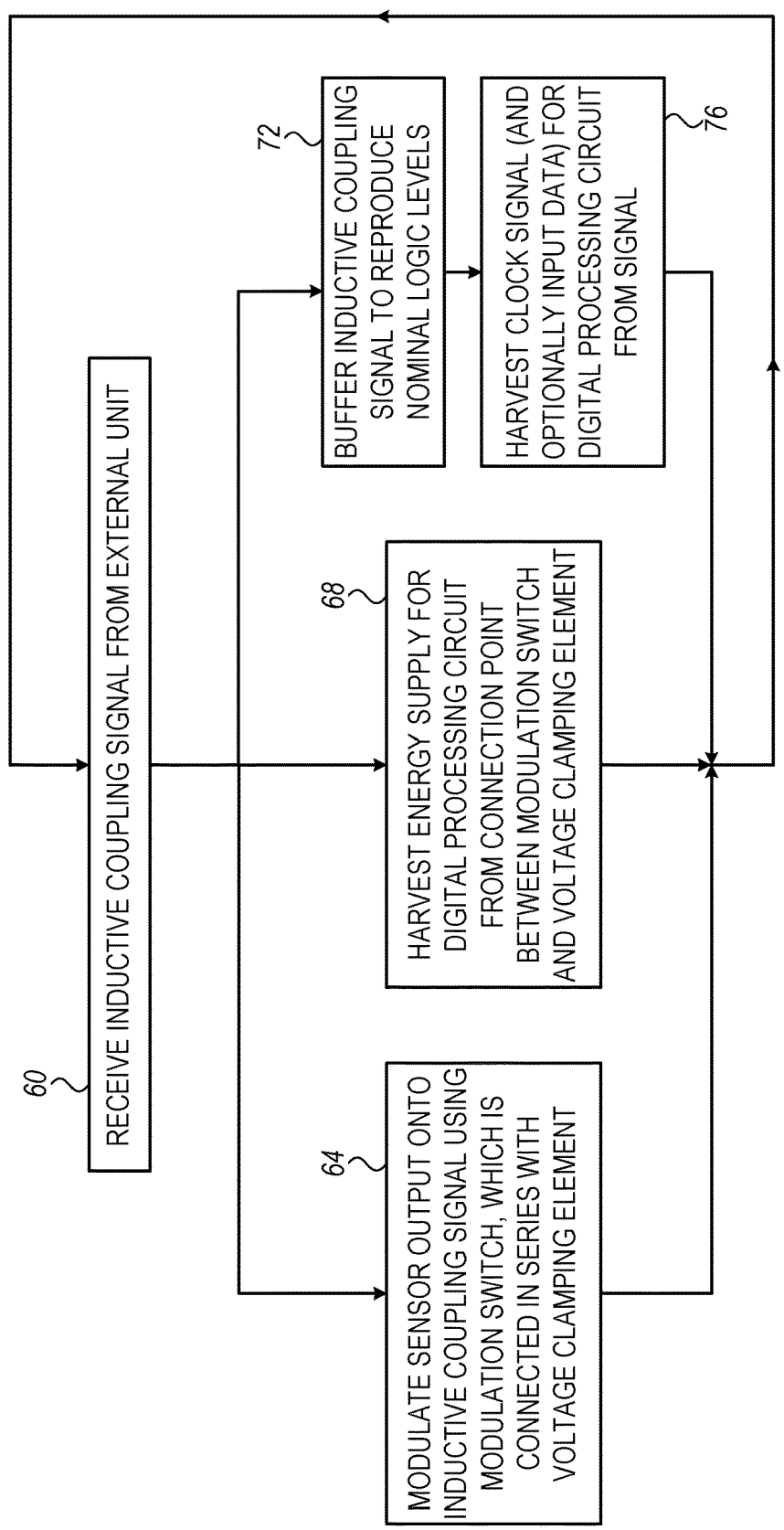
FIG. 2 is a flow chart that schematically illustrates a method for operating a system (e.g., an implant) for measuring pressures (e.g., sensing blood pressure in the cardiovascular system) remotely to an external unit, in accordance with an embodiment of the present invention.

FIG. 2 is a flow chart that schematically illustrates a method for operating implant 20, in accordance with an embodiment of the present invention. The method begins with front-end circuit 30 of implant 20 receiving the inductive coupling signal from the external unit, at an induction step 60.

At a load modulation step 64, digital processing circuit 28 modulates data, for transmission to the external unit, onto the inductive coupling signal by modulating switch 40. At an energy harvesting step 68, digital processing circuit 28 receives electrical power from the connection point between modulation switch 40 and voltage clamping element 44.

At a buffering step 72, buffer 48 buffers the "CLOCK & DATA IN" voltage signal. At a clock harvesting step 76, digital processing circuit 28 receives and uses the CLK signal from the output of buffer 48. In some embodiments, digital processing circuit 28 may also demodulate data sent from the external unit over this signal.

Figure 3:
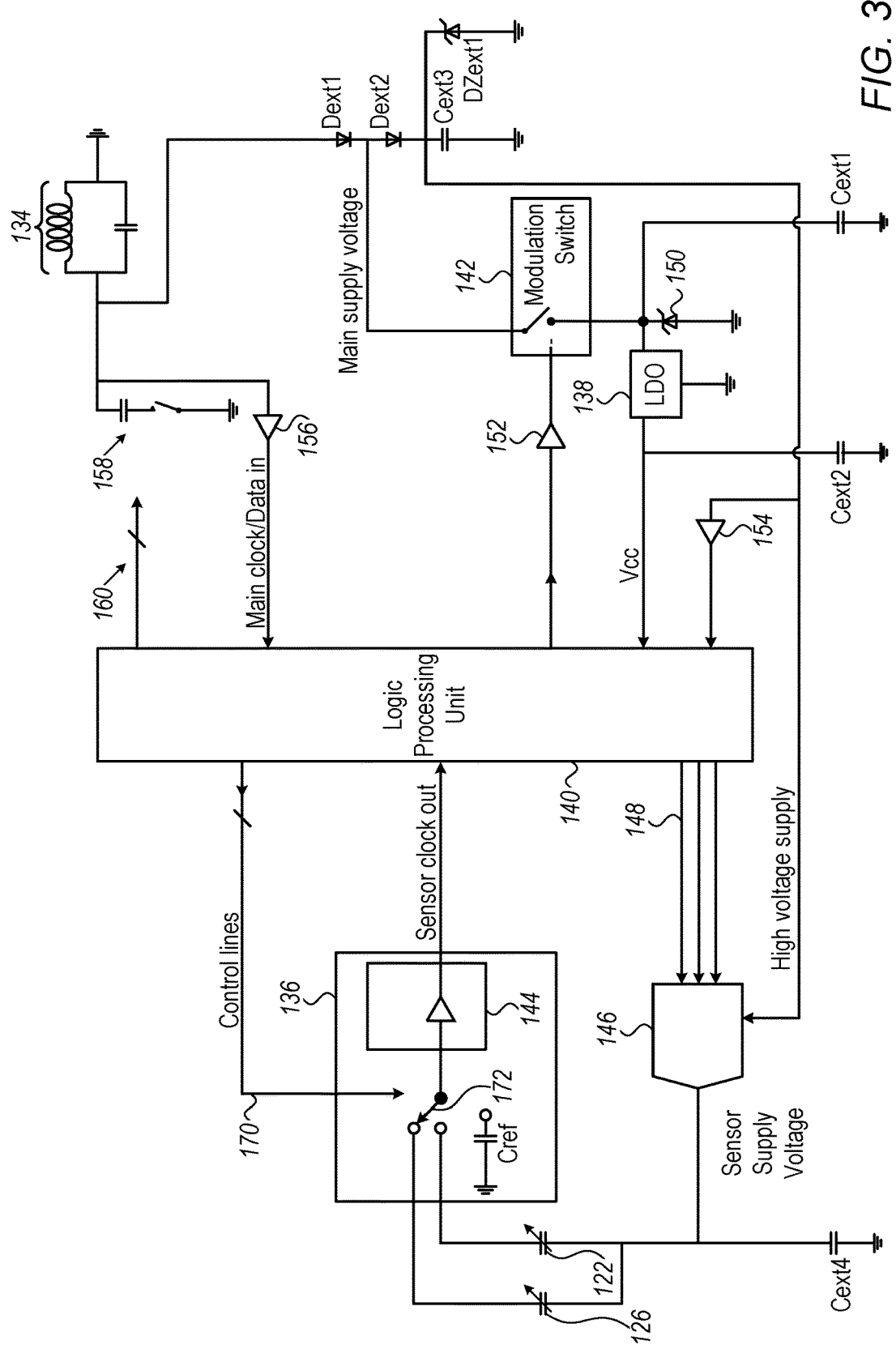
FIG. 3 is a block diagram that schematically illustrates an implant for sensing blood pressure in the cardiovascular system, in accordance with another embodiment of the present invention.

FIG. 3 is a block diagram that schematically illustrates an implant for sensing blood pressure in the cardiovascular system, in accordance with another embodiment of the present invention. The implant of FIG. 3 comprises an antenna 134, configured to, by drawing energy from the magnetic field generated by the external unit, provide a main supply voltage. The implant further comprises a capacitive pressure sensor 122, configured to vary its capacitance in response to the ambient pressure within the cardiovascular system.

In response to control signals 148 from a logic processing unit (LPU) 140, a voltage regulator 146 converts a high voltage supply, which is derived from the main supply voltage, into a direct current (DC) sensor-supply voltage, which supplies sensor 122. Voltage regulator 146 requires a certain minimum supply voltage in order to effectively supply voltage to the sensor. For example, in some embodiments, voltage regulator 46 requires at least 15.5 V. (Since this threshold is relatively high, relative to respective voltages required by other components of the implant, the voltage regulator supply voltage is referred to as a high voltage supply.) Voltage regulator 146 and sensor 122 may be collectively referred to as "operational circuitry."

The implant further comprises modulating circuitry that modulates the load of antenna 134. For example, the modulating circuitry may comprise an input-selecting-and-converting unit 136, LPU 140, and a modulation switch 142.

In an embodiment, input-selecting-and-converting unit 136 comprises conversion circuitry, which generates an output having a property that is a function of the capacitance that is input to the circuitry. For example, as shown in the figure, the conversion circuitry may comprise a capacitance-to-frequency converter 144. Converter 144 is an oscillator whose oscillation frequency depends on the capacitance that is input to the converter, such that the converter outputs a "sensor clock out" clock signal whose frequency is a function of the input. Stated differently, converter 144 converts the input capacitance into an output frequency.

Input-selecting-and-converting unit 136 further comprises an analog selector 172 that is configured to, in response to control signals 170 delivered over control lines from LPU 140, select an input to converter 144. FIG. 2 shows several possible inputs, as follows:

(i) The capacitance of sensor 122 may be input to converter 144, such that converter 144 converts the capacitance of the sensor into the output frequency.

(ii) The capacitance of a reference capacitor 126 may be input to converter 144, such that the converter converts the capacitance of the reference capacitor into the output frequency.

(iii) The capacitance of one or more calibration capacitors "Cref" may be input to converter 144, such that the converter converts the capacitance of the reference capacitor(s) into the output frequency.

In response to the "sensor clock out" signal, LPU 140 modulates the load of the antenna, by alternatingly connecting current-drawing circuitry to, and disconnecting the current-drawing circuitry from, the main supply voltage. When the current-drawing circuitry is connected to the main supply voltage, the load of the antenna is increased. Conversely, when the current-drawing circuitry is disconnected from the main supply voltage, the load of the antenna is decreased. The modulation in the load of the antenna causes variations in the amount of energy from the magnetic field consumed by the implant.

The external unit senses these variations, and computes, based on the variations, the input to converter 144. Thus, for example, LPU 140 may modulate the load of the antenna such as to indicate to the external unit the capacitance of—and hence, the pressure sensed by—sensor 122. The modulation in the load of the antenna also cause the main supply voltage to vary between a first, higher value, and a second, lower value. That is, when the current-drawing circuitry is disconnected from the main supply voltage, the main supply voltage has the first, higher value; conversely, when the current-drawing circuitry is connected to the main supply voltage, the main supply voltage has the second, lower value.

In some embodiments, the current-drawing circuitry comprises at least part of the modulating circuitry. In other words, in some embodiments, the modulating circuitry modulates the load of the antenna by alternatingly connecting the modulating circuitry to, and disconnecting the modulating circuitry from, the main supply voltage. For example, in the present embodiment, LPU 140 modulates the load of the antenna by controlling a modulation switch 142. In particular, by closing switch 142, LPU 140 increases the load of the antenna by connecting the LPU (and/or the input-selecting-and-converting unit) to the main supply voltage; conversely, by opening the switch, LPU 140 decreases the load of the antenna by disconnecting the LPU (and/or the input-selecting-and-converting unit) from the main supply voltage.

In an embodiment, a diode denoted Dext1 detects the envelope, thus deriving, the main supply voltage from the voltage across the antenna. In an example embodiment, the threshold supply voltage for the voltage regulator is assumed to be approximately 15.5 V, and correspondingly, the amplitude of the voltage across the antenna varies between approximately 3.5 V and 20 V. Due to a small voltage drop across diode Dext1, the amplitude of the main supply voltage varies between approximately 3 V and 19.5 V.

Typically, the circuitry within the implant further comprises a backup voltage source, such as a capacitor Cext3. When switch 142 is open and the main supply voltage has the first, higher value (e.g., 19.5 V), the backup voltage source derives a backup voltage from the main supply voltage. For example, Cext3 may derive the backup voltage, by charging. When switch 142 is closed and the main supply voltage has the second, lower value (e.g., 3 V), the backup voltage source supplies the backup voltage to the voltage regulator.

As noted above, if the opening of the modulation switch were to also disconnect the voltage regulator and sensor from the main supply voltage, the voltage across the antenna (and hence, the main supply voltage) would need to be significantly higher. For example, to ensure a threshold supply voltage of 15.5 V for the voltage regulator, the voltage across the antenna when loaded with the current-drawing circuitry would need to be approximately 20 V, and hence, the voltage across the antenna when unloaded might need to be approximately 40 V. (In contrast, in the example embodiment provided herein, the voltage across the antenna when unloaded is approximately 20 V.) To generate such high voltages, the antenna would need to be supplied with a large amount of energy.

Moreover, the supply of approximately 20 V to the LPU—which does not need such a large voltage, and which consumes a relatively large amount of current (e.g., 3 mAmp)—would lead to a large amount of excess power consumption. Hence, the placement of the modulation switch as shown herein is advantageous, in that (i) the voltage across the antenna may be relatively low (e.g., less than 22 V, such as approximately 20 V, as shown in FIG. 3B) when the current-drawing circuitry is disconnected from the main supply voltage, and/or (ii) when the current-drawing circuitry is connected to the main supply voltage, a much lower voltage—e.g., less than 5 V, such as approximately 3 V, as shown in FIG. 3B—may be supplied to the LPU.

It is noted that apparatus and techniques described herein may be applied to any alternative form of operational circuitry, any alternative form of modulating circuitry, and/or any alternative form of current-drawing circuitry. In other words, the scope of the present disclosure is not limited to the particular embodiments described herein, but rather, includes any relevant application in which there is a need to power both a relatively-high-voltage consumer (referred to herein as operational circuitry) and a lower-voltage-but-relatively-high-current consumer (referred to herein as current-drawing circuitry), while achieving sufficient antenna-modulation depth. For example, although the present description generally relates to sensor 122 as a capacitive pressure sensor, it is noted that the principles described herein may be applied to operational circuitry that comprises any type of sensor that is configured to sense any type of parameter. Similarly, the principles described herein may be applied to a sensor that is implanted in some portion of the anatomy other than the heart, to a sensor that is not implanted at all, as well as to operational circuitry that does not include a sensor at all.

Embodiments of the present invention also facilitate the operation of the current-drawing circuitry, even while the current-drawing circuitry is disconnected from the main supply voltage. For example, the LPU may operate on a DC voltage Vcc that is supplied by a low drop-off regulator (LDO) 138, which rectifies and regulates the main supply voltage. When switch 142 is open, LDO 138 is disconnected from the main supply voltage. Hence, to facilitate the operation of the LPU (and/or the input-selecting-and-converting unit) even while the switch is open, a second backup voltage source derives a second backup voltage from the main supply voltage, and, while the switch is open, supplies the second backup voltage to the LDO. For example, while the switch is closed, a capacitor Cext1 may charge, and subsequently, while the switch is open, supply voltage to the LDO. (Hence, LDO 138 is analogous to voltage regulator 146, while the second backup voltage source—e.g., Cext1—is analogous to the first backup voltage source—e.g., Cext3. While the switch is closed, the first backup voltage source supplies the voltage regulator, and while the switch is open, the second backup voltage source supplies the LDO.)

It is noted that the scope of the present disclosure includes the use of a backup voltage source for supplying voltage to the operational circuitry, as described above, even without the use of a backup voltage source for supplying voltage to the current-drawing circuitry. Similarly, the scope of the present disclosure includes the use of a backup voltage source for supplying voltage to the current-drawing circuitry, as described above, even without the use of a backup voltage source for supplying voltage to the operational circuitry.

In some embodiments, the implant further comprises a voltage clamping element 150, as explained above with respect to FIG. 1. Voltage clamping element 150 is drawn in FIG. 3 as a Zener diode purely for the sake of clarity. Element 150 may comprise any suitable kind of voltage clamping element, such as, for example, the element 44 of FIG. 1 above.

In an example embodiment, LPU 140 may draw varying amounts of current, depending on the current mode of operation of the LPU. Hence, without voltage clamping element 150, the second value of the main supply voltage would vary, depending on the current mode of operation of the LPU. To reduce this variation, the voltage clamping element draws an amount of current that varies inversely with the amount of current drawn by the LPU, such that, for example, the total amount of current drawn by the LPU and voltage clamping element together, while the switch is closed, is constant.

Various other components of the implant 24 are shown in FIG. 3, as follows:

(i) A diode Dext2 inhibits the discharging of Cext3, except for the purpose of supplying the voltage regulator.

(ii) A diode DZext1 provides overvoltage protection.

(iii) A capacitor Cext2 filters out noise from the voltage Vcc.

(iv) A capacitor Cext4 stabilizes the DC voltage supplied to the sensor.

(v) A "main clock/data in" signal, which is derived from the raw signal received from the external unit, provides a clock signal to the LPU, and further communicates data from the external unit. For example, via the "data in" signal, the external unit may request particular information from the LPU, which the LPU then provides, e.g., by selecting the appropriate input to capacitance-to-frequency converter 144, and then modulating the load of the antenna in response to the "sensor clock out" signal, as described above. The "main clock/data in" signal passes through a buffer 156, which adjusts the voltage of the signal to a level that is appropriate for the LPU.

(vi) A programmable resonance capacitor array 158 (depicted in FIG. 3, for simplicity, by only one capacitor) tunes the resonance capacitor in antenna 134, in response to signals 160.

(vii) A buffer 152 adjusts the voltage of the switch-controlling signal from the LPU to a level that is appropriate for switch 142.

(viii) A comparator 154 provides an indication to the LPU in the event that the voltage supply to voltage regulator 146 is not high enough. In response to the indication, the LPU communicates a signal to the external unit.

Although the embodiments described herein mainly address sensory medical implants, the methods and systems described herein can also be used in other devices and applications, such as in ultra-small actuators in medical devices, in built-in pressure sensors that evaluate the tension and fatigue in aircraft wings, bridges and other structures, in wireless pressure sensors for tires, and/or in remote temperature sensors for engines and various other machines, to name just a few possible examples.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
    a front-end circuit, which comprises an antenna and a modulation switch; and
    a digital processing circuit, which is configured to transmit data to a remote unit using inductive coupling of an Alternating Current (AC) magnetic field generated by the remote unit, by modulating a load impedance of the antenna using the modulation switch,
    wherein the front-end circuit is configured to supply to the digital processing circuit a voltage signal, which has a frequency of the AC magnetic field and which has a non-zero envelope both during intervals in which the modulation switch is closed and during intervals in which the modulation switch is open, and wherein the digital processing circuit is configured to derive a clock signal from the voltage signal.

2. The apparatus according to claim 1, wherein the front-end circuit comprises a voltage clamping element connected in series with the modulation switch.

3. The apparatus according to claim 2, wherein the front-end circuit further comprises a diode connected in series with the modulation switch.

4. The apparatus according to claim 2, wherein the antenna is connected in parallel to the serially-connected modulation switch and voltage clamping element.

5. The apparatus according to claim 2, wherein the voltage clamping element is configured to clamp a voltage signal induced by the AC magnetic field across the antenna, and wherein the front-end circuit is configured to provide the clamped voltage signal for powering the digital processing circuit from a connection point between the modulation switch and the voltage clamping element.

6. The apparatus according to claim 2, wherein the voltage clamping element comprises a transistor biased by a Zener diode.

7. The apparatus according to claim 1, wherein the digital processing circuit is configured to derive the clock signal solely from the voltage signal without an oscillator and/or a Phase-Locked Loop (PLL).

8. The apparatus according to claim 1, and comprising a pressure sensor, wherein the digital processing circuit is configured to read a pressure reading from the pressure sensor, and to transmit the pressure reading to the remote unit using the derived clock signal.

9. The apparatus according to claim 1, wherein the antenna comprises a coil.

10. The apparatus according to claim 9, wherein the front-end circuit comprises a capacitor connected in parallel with the coil.

11. The apparatus according to claim 1, wherein the digital processing circuit is configured to modulate the load impedance by alternately opening and closing the modulation switch in a pattern that depends on the data.

12. The apparatus according to claim 1, wherein the digital processing circuit is configured to derive the clock signal from the voltage signal both during the intervals in which the modulation switch is closed and during the intervals in which the modulation switch is open.

13. A method, comprising:
    using a digital processing circuit, transmitting data to a remote unit using inductive coupling of an Alternating Current (AC) magnetic field generated by the remote unit, by modulating a load impedance of an antenna using a modulation switch;
    supplying to the digital processing circuit a voltage signal, which has a frequency of the AC magnetic field and which has a non-zero envelope both during intervals in which the modulation switch is closed and during intervals in which the modulation switch is open; and in the digital processing circuit, deriving a clock signal from the voltage signal.

14. The method according to claim 13, wherein modulating the load impedance and supplying the voltage signal are performed by a front-end circuit that comprises a voltage clamping element connected in series with the modulation switch.

15. The method according to claim 14, wherein the front-end circuit further comprises a diode connected in series with the modulation switch.

16. The method according to claim 14, wherein the antenna is connected in parallel to the serially-connected modulation switch and voltage clamping element.

17. The method according to claim 14, and comprising clamping, using the voltage clamping element, a voltage signal induced by the AC magnetic field across the antenna, and providing the clamped voltage signal for powering the digital processing circuit from a connection point between the modulation switch and the voltage clamping element.

18. The method according to claim 14, wherein the voltage clamping element comprises a transistor biased by a Zener diode.

19. The method according to claim 13, wherein deriving the clock signal is performed solely from the voltage signal without an oscillator and/or a Phase-Locked Loop (PLL).

20. The method according to claim 13, and comprising reading a pressure reading from a pressure sensor, and transmitting the pressure reading to the remote unit using the derived clock signal.

21. The method according to claim 13, wherein the antenna comprises a coil.

22. The method according to claim 21, wherein a capacitor is connected in parallel with the coil.

23. The method according to claim 13, wherein modulating the load impedance comprises alternately opening and closing the modulation switch in a pattern that depends on the data.

24. The method according to claim 13, wherein deriving the clock signal from the voltage signal is performed both during the intervals in which the modulation switch is closed and during the intervals in which the modulation switch is open.

25. A method, comprising:
applying an external unit to form a magnetic field, having a frequency and an accuracy, around a remote system comprising a modulation switch and a digital processing circuit;
in the remote system, deriving from the magnetic field a clock signal having the frequency and the accuracy;
applying the digital processing circuit to generate a digital signal carrying data synchronized with the clock signal;
applying the digital processing circuit to manipulate the modulation switch in a series of alternations between an open state and a closed state in a pattern derived from the digital signal, thereby encoding the data by way of load modulation; and
applying the external unit to decode the data by extracting the load modulation with the clock signal.

26. The method of claim 25, and comprising powering the digital processing circuit solely from the magnetic field by way of inductive coupling.

27. The method according to claim 25, wherein deriving the clock signal is performed both during intervals in which the modulation switch is in the closed state and during intervals in which the modulation switch is in the open state.

28. The method according to claim 25, a voltage clamping element is connected in series with the modulation switch.

29. The method according to claim 28, wherein a diode is connected in series with the modulation switch.

30. The method according to claim 28, wherein an antenna of the remote system is connected in parallel to the serially-connected modulation switch and voltage clamping element.

31. The method according to claim 28, and comprising clamping, using the voltage clamping element, a voltage signal induced by the magnetic field across the antenna, and providing the clamped voltage signal for powering the digital processing circuit from a connection point between the modulation switch and the voltage clamping element.

* * * * *